United States Patent [19]
McCary

[11] Patent Number: 5,964,746
[45] Date of Patent: Oct. 12, 1999

[54] MICROSURGICAL SYSTEM HAVING ISOLATED HANDPIECE DETECTION APPARATUS

[75] Inventor: Brian Douglas McCary, St. Louis, Mo.

[73] Assignee: Bausch & Lomb Surgical, Inc., Claremont, Calif.

[21] Appl. No.: 08/919,687

[22] Filed: Aug. 28, 1997

Related U.S. Application Data

[60] Provisional application No. 60/025,498, Aug. 29, 1996.

[51] Int. Cl.$^6$ ................................................ A61B 17/00
[52] U.S. Cl. .............................. 606/1; 606/174; 606/205
[58] Field of Search ............................. 606/1, 51, 170, 606/174, 205; 604/22

[56] References Cited

U.S. PATENT DOCUMENTS 5,249,121  9/1993  Baum et al. ................................. 606/1

Primary Examiner—Michael Buiz
Assistant Examiner—Julian W. Woo
Attorney, Agent, or Firm—Senniger,Powers,Leavitt & Roedell; Grant D. Kang; Rita D. Vacca

[57] ABSTRACT

A system for controlling a plurality of ophthalmic microsurgical instruments is disclosed. Particularly, the present invention includes an ophthalmic handpiece, such as an intraocular surgical scissors or forceps, which is electrically isolated from the electric power source for controlling electrical hardware by a transformer. In a preferred embodiment, the handpiece is removably attachable to the electric control handpiece and is interchangeable with other ophthalmic handpieces. Furthermore, an apparatus to detect the presence of the interchangeable handpiece when it is connected to the controlling electric hardware is provided.

12 Claims, 2 Drawing Sheets

Microfiche Appendix Included
(32 Microfiche, 6090 Pages)

MICROSURGICAL SYSTEM HAVING ISOLATED HANDPIECE DETECTION APPARATUS

MICROFICHE APPENDIX

This application includes a microfiche appendix which is a copy of the provisional application Ser. No. 60/025,498 filed Aug. 29, 1996 under which priority is claimed.

BACKGROUND OF THE INVENTION

This invention relates generally to microsurgical and ophthalmic systems and, particularly, to circuitry for operating and controlling a variety of handpieces and probe adapted to function as, for example, intraocular scissors or forceps, which handpieces are electrically isolated for circuitry activated by foot pedal controls.

Present day ophthalmic microsurgical systems provide one or more surgical instruments connected to a control console. The instruments are often electrically or pneumatically operated and the control console provides electrical or fluid pressure control signals for operating the instruments. The control console usually includes several different types of human actuable controllers for generating the control signals supplied to the surgical instruments. Often, the surgeon uses a foot pedal controller to remotely control the surgical instruments.

The use of intraocular surgical handpiece instruments functioning as scissors or forceps is well known in the art. While manually operated ophthalmic scissors and forceps are still in use worldwide, they suffer from the disadvantage of being subject to human limitations for speed and accuracy. Therefore, the use of surgical scissors and forceps having electric drive means, whether it be a solenoid, stepper motor or direct current motor, has become increasingly widespread.

Prior art circuits for electrically controlled intraocular surgical handpieces that are removable from common controlling hardware have included an apparatus for sensing the presence of the handpiece, but the handpiece and the sensing apparatus have been connected to the electrical power source, thereby operating in a grounded patient configuration. Such prior art circuit configurations leave a patient vulnerable to injury from the power source of the ophthalmic surgical hardware in the event that the hardware is electrically defective. Such configurations also leave a patient vulnerable to injury form the power sources of any electrically defective equipment that may be being used in conjunction with the ophthalmic surgical hardware.

SUMMARY OF THE INVENTION

It is in view of the above problems that the present invention was developed. The present invention includes an ophthalmic handpiece, such as an intraocular surgical scissor or forceps, which is electrically isolated from the electric power source of controlling electrical hardware by a transformer. In a preferred embodiment, the handpiece is removably attachable to the electrical control hardware and is interchangeable with other ophthalmic handpieces. Furthermore, an apparatus to detect the presence of the interchangeable probe when it is connected to the controlling electric hardware is provided.

In a preferred embodiment, the detection apparatus comprises a conventional opto-isolator circuit chip containing a photo diode in optical communication with photo-detect circuitry. The anode of the photo diode is connected to the isolated output of the drive circuit, while the output of the photo-detect circuitry is connected to ground. The detection circuit includes a direct current signal source, a resistor connected between the direct current signal source and the input to the photo-detect circuit, and an output signal line connected between the input to the photo-detect circuit and control software. When a handpiece is connected to the controlling electrical hardware, a shorting bar in the handpiece connects the cathode of the photo diode to isolated ground, causing the photo diode to emit light. This, in turn, activates the photo-detect circuitry in the chip, thereby altering the output signal by allowing the signal generated by the direct current signal source to pass through the photo-detect circuit to ground. This alteration of the output signal causes the control software in electrical communication therewith to close a relay, such as an electric or electromechanical switch, thereby enabling power from the electric power source to pass through the primary coil of the transformer and drive the ophthalmic handpiece.

The present invention further includes a first method for detecting the presence of an ophthalmic handpiece. The method includes the steps of applying a first direct current signal to the anode of the photo diode of an opto-isolator, applying a second direct current signal to the photo-detect circuitry of the opto-isolator, and receiving an output signal from the photo-detect circuitry of the opto-isolator determined by whether the cathode of the photo diode is connected to isolated ground. The method may also include the step of activating a switch in response to receiving the appropriate output signal to bring an electric power source into electrical communication with the detected ophthalmic probe.

In another embodiment, the detection apparatus comprises a second transformer which may have a resistor connected across its secondary winding and a detection circuit connected to its primary winding. The detection circuit includes a comparator which measures the electrical input signal to determine whether the handpiece is connected. When the handpiece is connected, a shorting bar in the handpiece is connected across the secondary winding of the second transformer, changing the signal measured by the comparator to a predetermined value corresponding to the presence of the handpiece. In response thereto, the comparator directs the control software in electrical communication therewith to close a relay in the same manner as discussed above.

The present invention further includes a second method for detecting the presence of an ophthalmic handpiece. The method includes the steps of applying a first alternating current signal to the primary winding of a transformer, receiving a second alternating current signal determined by the reflected impedance of the load at the secondary winding of the transformer, and comparing the second alternating current signal to a standard to determine whether the probe is connected. The method may also include the step of activating a switch in response to receiving the appropriate second alternating current signal to bring an electric power source into electrical communication with the detected ophthalmic probe.

Use of an isolated ophthalmic handpiece of this invention provides increased patient safety. Furthermore, a device of the present invention allows recognized safety standards, such as the voluntary standard IEC601-1 promoted by the International Electrotechnical Commission, Underwriters Laboratory standard UL2601 and the European Union standard EN60601-1, to be met.

It is, therefore, a principal object of the present invention to teach the construction and operation of an electrically controlled ophthalmic handpiece that is electrically isolated form a non-battery power source of electrical control hardware to provide improved patient safety.

It is another object of the invention to provide an ophthalmic handpiece electrically isolated from a power source that does not need to be recharged over time.

It is another object of the invention to provide an ophthalmic handpiece electrically isolated from a power supply that reduces the need for user maintenance.

It is another object of the invention to provide an electrically isolated ophthalmic handpiece that is removably attachable to the electrical control hardware.

It is another object of the invention to provide an electrically isolated ophthalmic handpiece that is interchangeable from the electrical control hardware with other ophthalmic handpieces.

It is another object of the invention to provide apparatus for detecting the presence of an electrically isolated detachable ophthalmic handpiece.

It is another object of the invention to provide apparatus for detecting the presence of, and identifying, any of a variety of interchangeable electrically isolated detachable ophthalmic handpieces.

It is another object of the invention to provide apparatus for detecting the presence of, and identifying, any of a variety of interchangeable electrically isolated detachable ophthalmic handpieces and, in response thereto, activate a switch to bring an electric power source into electrical communication with the detected ophthalmic probe.

It is another object of the invention to provide methods for detecting the presence of an electrically isolated removable ophthalmic handpiece.

It is another object of the invention to provide methods for detecting the presence of, and identifying, any of a variety of interchangeable electrically isolated removable ophthalmic handpieces.

It is another object of the invention to provide methods for detecting the presence of, and identifying, any of a variety of interchangeable electrically isolated removable ophthalmic handpieces and, in response thereto, activate a switch to bring an electric power source into electrical communication with the detected ophthalmic probe.

DETAILED DESCRIPTION OF PREFERRED EMBODIMENTS

Figure 1:
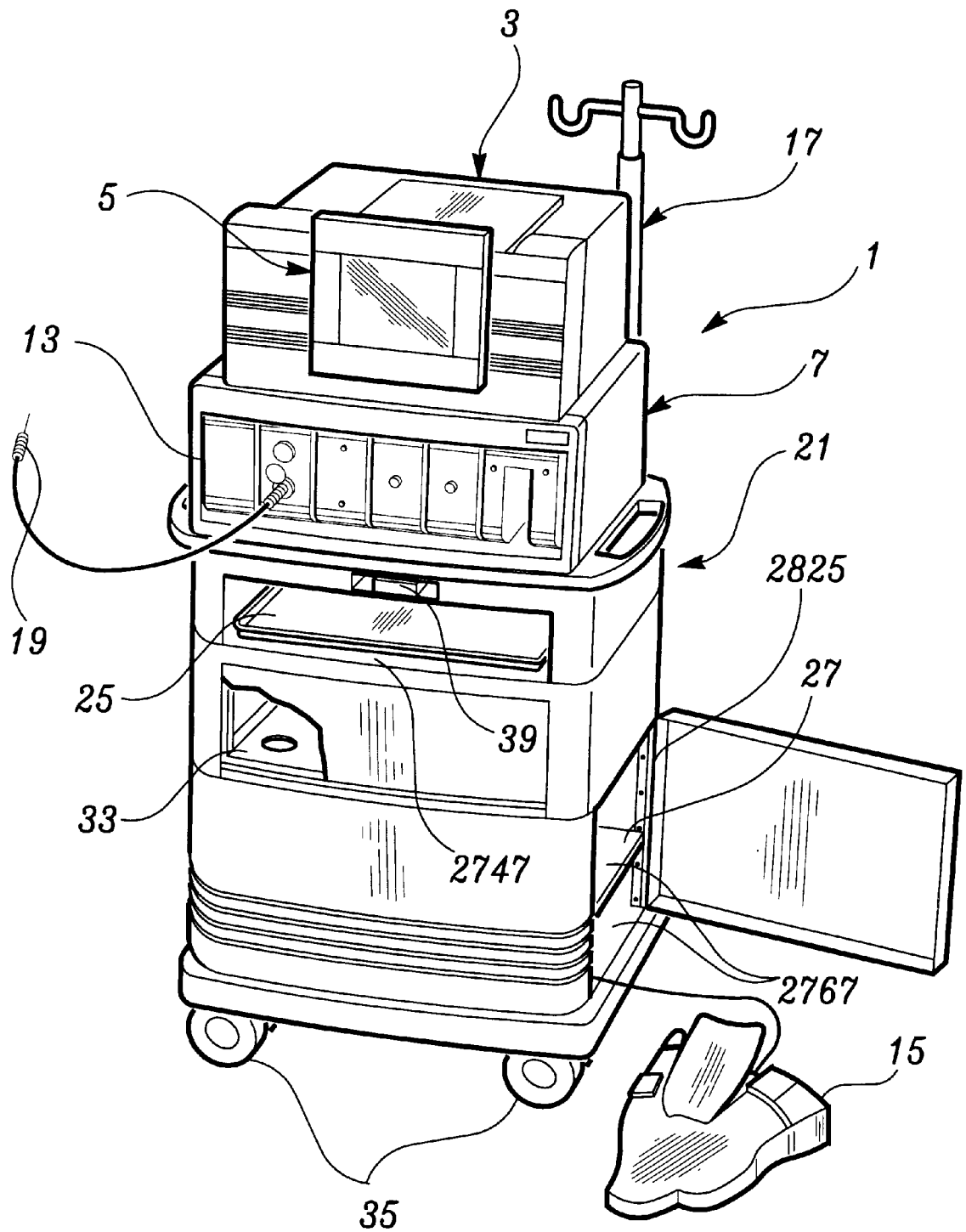
FIG. 1 is a perspective view of a microsurgical control system for use with ophthalmic microsurgical instruments, and having a plurality of control modules utilizing a variety of surgical handpieces in accordance with the present invention.

Referring to the accompanying drawings in which like reference numbers indicate like elements, FIG. 1 an ophthalmic microsurgical control system 1 for use with various ophthalmic microsurgical instruments 19. Control system 1 includes a computer unit 3 having a flat panel display 5, a base unit 7 having a plurality of modules 13, and peripherals such as a foot control assembly 15 and a motorized intravenous (IV) pole assembly 17. Each of the modules 13 housed in the base unit 7 controls at least one ophthalmic microsurgical instrument 19 for use by a surgeon in performing various ophthalmic surgical procedures.

As is well known in the art, ophthalmic microsurgery involves the use of a number of different instruments 19 for performing different functions. These instruments 19 include vitrectomy cutters, Phacoemulsification or phacofragmentation handpieces, electric microscissors, fiber optic illumination instruments, coagulation handpieces and other microsurgical instruments known in the art. To optimize performance of instruments 19 during surgery, their operating parameters differ according to, for example, the particular procedure being performed, the different stages of the procedure, the surgeon's personal preferences, whether the procedure is being performed in the anterior or posterior portion of the patient's eye, and so on.

As shown in FIG. 1, an instrumentation cart, generally designated 21, supports system 1. Preferably, the cart 21 includes a surgical, or Mayo, tray 25, the automated IV pole assembly 17, a storage compartment 27 for stowing the foot control assembly 15, disposable packs and other items, an opening 33 to house an expansion base unit (not shown in FIG. 1), and rotating casters 35. Base unit 7 and computer unit 3 preferably sit on top of instrumentation cart 21 as shown in FIG. 1 and the Mayo tray 25 is mounted on an articulating arm (not shown) preferably attached to the top of instrumentation cart 21, directly beneath base unit 7. Instrumentation cart 21 also holds a remote control transmitter, generally indicated 39, for use in remotely controlling system 1.

The modules 13 in base unit 7 house control circuits for the various microsurgical instruments 19 so that the system's user is able to configure system 1 for optimizing its use by the surgeon. Modules 13 include connections or ports by which one or more microsurgical instruments 19 connect to each module 13 and house the necessary control circuitry for controlling operation of the particular instrument or instruments 19 connected thereto. Thus, the user, by inserting the desired modules 13 in base unit 7, configures system 1 to meet a particular surgeon's preference, to control each of the instruments 19 needed for a particular surgical procedure, or to otherwise optimize system 1 for use by the surgeon.

Figure 2:
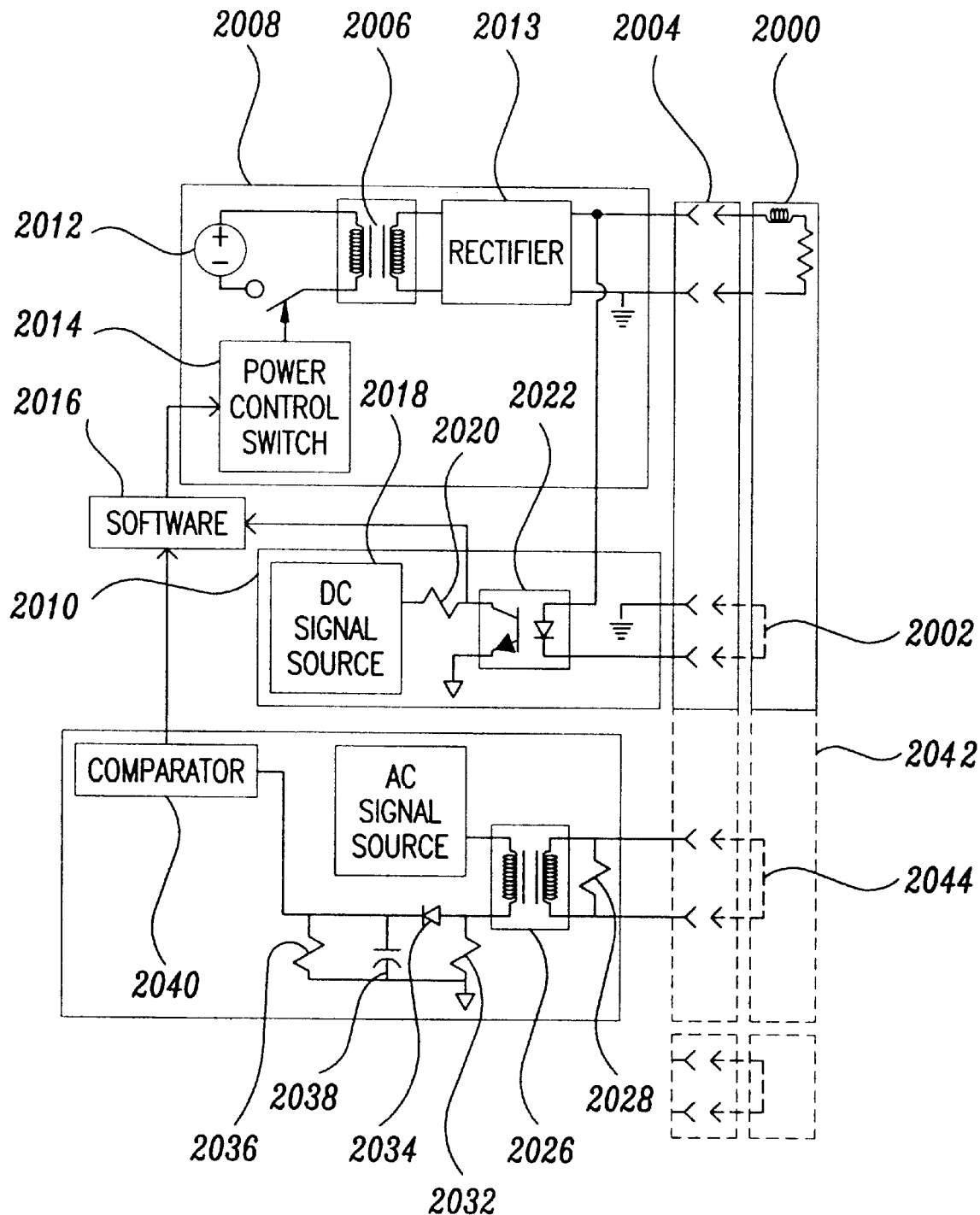
FIG. 2 is a circuit diagram of the invention showing two embodiments of electrically isolated detection apparatus.

Referring now to FIG. 2 which illustrates a preferred embodiment of the present invention which has an isolated, floating patient configuration. An ophthalmic handpiece or probe 2000 of conventional design such as those produced by Storz Instrument Company, e.g., an intraocular surgical scissor or forceps, includes a shorting bar 2002. The probe 2000 is removably attached to a connector 2004, bringing the probe 2000 into electrical communication with the secondary winding of a conventional power transformer 2006 of a power circuit 2008, while simultaneously bringing the shorting bar 2002 into electrical communication with a first detection circuit 2010. Preferably, probe 2000 is one of microsurgical instruments 19 for use with system 1. In this regard, connector 2004 comprises a port on the front cover of a scissors module (not shown).

The transformer 2006 has its primary winding connected to a direct current power source 2012. A rectifier 2013 having two output terminals is connected across the secondary winding of the transformer 2006. The rectifier 2013 delivers a direct current power signal across one of its output terminals to the load, while its other output terminal may be connected to isolated ground. In this way, direct current power is provided to the probe 2000 while the probe 2000 remains electrically isolated from the electric power source 2012.

A power control switch or relay 2014 is connected between the power source 2012 and the transformer 2006, and is controlled by software 2016 activated by a signal from the first detection circuit 2010. In this instance, a NEURON™ processor of a scissors module executes software 2016 for controlling the operation of probe 2000. The relay 2014 may be any conventional electrical or electromechanical switch capable of alternately interrupting and reestablishing electrical power to the primary coil of the transformer 2006.

The first detection circuit 2010 includes a direct current signal source 2018 which generates a signal across a first resistor 2020 and into the input of photo-detection circuitry of a first opto-isolator 2022. The photo diode of the first opto-isolator 2022 is in optical communication with, and electrically isolated from, the photo-detection circuitry. In a first embodiment, the photo diode has its anode connected to a second isolated power supply consisting of transformer 2019 and a rectifier 2021 for providing current to operate the photo diode. In a second embodiment, (not shown in FIG. 2), the cathode of the photo diode is connected to ground. The photo-detection circuit of the first opto-isolator 2022 has its output connected to ground, and its input connected to the output of the first detection circuit 2010. It is the signal generated from the output of the first detection circuit 2010 that activates the software 2016. In a preferred embodiment, the first signal source 2018 emits a direct current signal of five volts.

In the first embodiment, when the handpiece 2000 is connected to the power circuit 2008, the shorting bar 2002 connects the cathode of the photo diode of the first opto-isolator 2022 to isolated ground, thereby causing the photo diode to emit light. Alternatively, in the second embodiment, when the handpiece 2000 is connected to the power circuit 2008, the shorting bar 2002 connects the anode of the photo diode of the first opto-isolator 2022 to the electrically isolated output of the power circuit 2008, thereby causing the photo diode to emit light. This, in turn, activates the photo-detect circuitry in the first opto-isolator chip 2022, thereby altering the output signal by allowing the signal generated by the first direct current signal source 2018 to pass through the photo-detect circuit to ground. This alteration of the output signal from the first detection circuit 2010 causes the control software 2016 in electrical communication therewith to close the power control relay 2014, thereby enabling power from the electric power source 2012 to pass through the primary coil of the transformer 2006 and drive the ophthalmic handpiece 2000. In this way, the first detection circuit 2010 can detect when the handpiece 2000 is connected to the power circuit 2008 and cause the power circuit 2008 to deliver driving power to the handpiece 2000 while the first detection circuit 2010 remains electrically isolated form the handpiece 2000.

A second embodiment for a detection circuit 2024 is shown in FIG. 2 and can be used alternatively to, or in conjunction with, the first detection circuit 2010. The second detection circuit 2024 includes a second transformer 2026 having a second resistor 2028 (10k ohms) connected across its secondary coil. The second transformer 2026 is a conventional transformer having a 1:1 ratio between its primary and secondary windings, although transformers having different ratios may be used. An alternating current signal source 2030 provides a signal to one end of the primary winding of the second transformer 2026. The opposing end of the primary winding is connected to ground through a third resistor 2032 (1k ohms). The opposing end of the primary winding of the second transformer 2026 is also connected to the anode of a diode 2034 (1N918, 1N4148 or similar diode). A fourth resistor 2036 (100k ohms) and a capacitor 2038 (0.01 mfarads) are connected in parallel between the cathode of the diode 2034 and ground. A comparator 2040, having its input connected to the cathode of the diode 2034, compares the received signal with a standard signal to determine the presence of a second probe 2042. When the second probe 2042 having a second shorting bar 2044 is connected to the power circuit 2008, the second shorting bar 2044 is connected across the second resistor 2028 of the second detection circuit 2024. This causes the comparator 2040 to provide an output signal to the control software 2016 which, in turn, causes the power control switch 2014 to close to provide direct current electrical power to drive the second handpiece 2042. Alternatively, the comparator 2040 can be connected directly to the relay 2014 so that the output signal from the comparator 2040 will activate the relay 2014.

In operation of the second detection circuit 2024, an alternating current signal, such as a 5 volt, 62.5 hertz square wave, is provided by the alternating current signal source 2030 to the primary winding of the second transformer 2026. When the second handpiece 2042 is not connected, the reflected impedance of the load provided by the second resistor 2028 on the secondary winding side of the second transformer 2026 is relatively high, and the voltage at the anode of the diode 2034 is insufficient to forward bias the diode 2034. Consequently, the signal received by the comparator 2040 is essentially zero, indicating that the second probe 2042 is not connected.

When the second handpiece 2042 is connected to the power circuit 2008, the second shorting bar 2044 is connected across the secondary winding of the second transformer 2026, causing the reflected impedance of the load on the secondary winding of the second transformer 2024 to be relatively low. As a result, a higher voltage is measured by the second detection circuit 2024. This higher voltage at the anode of the diode 2034 is sufficient to forward bias the diode 2034 to provide a rectified, filtered signal to the comparator 2040. The signal is then compared to a standard signal. If the comparator 2040 determines that the second probe 2024 is connected, the comparator 2040 sends a corresponding signal in response thereto to the controlling software 2016. The software 2016 then directs the power control switch 2014 to close, enabling the direct current power from the power source 2012 to drive the second probe 2042. In this way, the second detection circuit 2024 can detect when the second handpiece 2042 is connected to the power circuit 2008 and cause the power circuit 2008 to deliver driving power to the handpiece 2042 while the second detection circuit 2024 remains electrically isolated form the handpiece 2000.

It should be recognized that the selected values for the resistors, capacitor and other components, as well as for the stated voltage, are provided for illustration of the invention and not as the only functioning combination. The values of each may be changed without changing the invention.

The present invention can be designed to have only one electrically isolated detection circuit, thereby being able to detect when a probe is present, but not being able to identify the probe. In a preferred embodiment, the present invention includes multiple electrically isolated detection circuits, each detection circuit corresponding to a specific probe or handpiece. In this embodiment, the connector 2004 includes multiple shorting bar connection ports, each shorting bar connection port serving to detachably connect the shorting bar of a specific type of ophthalmic handpiece with a specific detection circuit, (as shown in dotted line in FIG. 2). As a result, the software 2016 can now not only determine the when a probe is connected to the power circuit 2008, but it can also identify the connected probe by determining which probe corresponds to the detection circuit sending the output signal to the software 2016. The multiple detection circuits can be electrically isolated from their corresponding handpiece by using an opto-isolator in each detection circuit, by using a transformer in each detection circuit, or by using an opto-isolator in some of the detection circuits and a transformer in the others. In a preferred embodiment, each detection circuit is optically isolated from the probe because an opto-isolator occupies less space and weighs less than a transformer.

The present invention further includes a first method for detecting when an ophthalmic handpiece or probe is removably connected to controlling electrical hardware. The first method includes the steps of providing a first direct current electric signal to the input of the photo-detection circuitry of an opto-isolator, providing a second direct current electric signal to the anode of the photo diode, and receiving an output signal from the opto-isolator, the state of the output signal being determined by whether the cathode of the photo diode is connected to isolated ground. The method may also include the step of activating a switch or relay when the handpiece is detected to bring the power source into electrical communication with the detected handpiece.

The present invention further includes a second method for detecting when an ophthalmic probe is removably connected to a power circuit. The second method includes the steps of providing an alternating current signal to the input of the primary winding of a transformer, receiving an output signal from the output of the primary winding, the output signal being determined by the reflected impedance of the load on the secondary winding of the transformer, and comparing the output signal to a predetermined standard signal to determine whether a handpiece is connected. The method may also include the step of activating a switch or relay when the handpiece is detected to bring the power source into electrical communication with the detected handpiece.

The electrical isolation provided by the transformer of the power circuit in conjunction with the opto-isolator or, alternatively, the second transformer of the detection circuit allows the power circuit to provide power to the handpiece, and the detection circuit to sense the presence of the handpiece, respectively, while maintaining the integrity of the isolated patient configuration. As a result, the chances of a patient being injured due to electrical malfunctions in hardware being used in conjunction with the handpiece, as well from electrical malfunctions within the handpiece and its controlling hardware are reduced, improving patient safety.

It should be recognized that the selected values for the components (transformer ratings, resistor values, diode types, etc.), as well as for the stated voltages and current, are provided for illustration of the invention and not as the only functioning combination. The values of each may be changes without changing the invention.

In view of the foregoing, it will be seen that the several objects of the invention are achieved and other advantages are attained. Furthermore, as various modifications could be made in the constructions herein described and illustrated without departing from the scope of the invention, it is intended that all material contained in the foregoing description or shown in the accompanying drawings should be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. An apparatus for detecting when an ophthalmic handpiece is connected to a power circuit in a patient-isolated configuration comprising:

an opto-isolator having a photo diode in optical communication with a photo-detection circuit having an input and an output;

a first direct current signal source connected to the input of the photo-detection circuit;

a second direct current signal source electrically isolated from the first direct current signal source and connected to the anode of the photo diode when the ophthalmic handpiece is connected to the power circuit; and a direct current output signal connected to the input of the photo-detection circuit.

2. The apparatus of claim 1 wherein a shorting bar is connected between the cathode of the photo diode and an isolated ground when the ophthalmic handpiece is connected to the power circuit.

3. The apparatus of claim 1 wherein the power circuit includes a switch for opening and closing the power circuit and wherein the direct current output signal controls the state of the switch in accordance with whether an ophthalmic handpiece is connected to the power circuit.

4. An apparatus for detecting when an ophthalmic scissor or forcep is connected to a power circuit in a patient-isolated configuration comprising:

a transformer having primary and secondary windings;

an alternating current signal source connected to the input of the primary winding of the transformer; and a comparator in electrical communication with the output of the primary winding of the transformer to compare the signal received to a standard signal to determine whether an ophthalmic scissor or forcep is connected to the power circuit.

5. The apparatus of claim 4 wherein the power circuit includes a switch for opening and closing the power circuit and wherein the comparator generates a signal to control the state of the switch in accordance with whether an ophthalmic scissor or forcep is connected to the power circuit.

6. The apparatus of claim 4 wherein a shorting bar is connected across the secondary winding of the transformer when a scissor or forcep handpiece is connected to the power circuit.

7. A method for detecting, in a patient-isolated configuration, when an ophthalmic handpiece is removably connected to a power circuit including a power control switch, the method comprising the steps of:

providing a first direct current signal to the input of a photo-detection circuit in optical communication with a photo diode;

providing a second direct current signal to the anode of the photo diode, the second direct current signal being electrically isolated from the first direct current signal; and receiving an output signal from the input of the photo-detection circuit that varies in accordance with whether a handpiece is connected to the power circuit.

8. The method of claim 7 further comprising the step of closing the power control switch when the output signal indicates that an ophthalmic handpiece is connected to the power circuit.

9. The apparatus of claim 7 further comprising the step of connecting the cathode of the photo diode to isolated ground when an ophthalmic handpiece is connected to the power circuit.

10. A method for detecting, in a patient-isolated configuration, when an ophthalmic scissor or forcep handpiece is removably connected to a power circuit including a power control switch, the method comprising the steps of:

providing an alternating current signal to the primary winding of a transformer;

receiving an output signal from the primary winding of the transformer, the output signal varying as determined by the reflected impedance of the load on the secondary winding of the transformer; and comparing the output signal to a predetermined standard signal to determine whether an ophthalmic scissor or forcep handpiece is connected to the power circuit.

11. The method of claim 10 further comprising the step of closing the power control switch when the output signal indicates that an ophthalmic scissor or forcep handpiece is connected to the power circuit.

12. The apparatus of claim 10 further comprising the step of connecting a shorting bar across the secondary winding of the transformer when an ophthalmic handpiece is connected to the power circuit.

* * * * *